(12) United States Patent
Chuang et al.

(10) Patent No.: US 11,898,147 B2
(45) Date of Patent: Feb. 13, 2024

(54) CPG-OLIGODEOXYNUCLEOTIDE COMPOUNDS IN COMBINATION WITH IMMUNE MODULATORS FOR CANCER IMMUNOTHERAPY

(71) Applicant: National Health Research Institutes, Zhunan Township (TW)

(72) Inventors: Tsung-Hsien Chuang, Zhunan Township (TW); Jen-Chih Tseng, Zhunan Township (TW); Jing-Xing Yang, Zhunan Township (TW); Yi-Ling Liu, Zhunan Township (TW)

(73) Assignee: NATIONAL HEALTH RESEARCH INSTITUTES, Zhunan Town (TW)

( * ) Notice: Subject to any disclaimer, the term of this patent is extended or adjusted under 35 U.S.C. 154(b) by 121 days.

(21) Appl. No.: 17/467,390

(22) Filed: Sep. 6, 2021

(65) Prior Publication Data

US 2023/0075652 A1    Mar. 9, 2023

(51) Int. Cl.
| | | |
|---|---|---|
| *C07H 21/02* | (2006.01) | |
| *C12N 15/117* | (2010.01) | |
| *C07K 16/28* | (2006.01) | |
| *A61P 35/00* | (2006.01) | |
| *A61K 31/711* | (2006.01) | |

(52) U.S. Cl.
CPC .......... *C12N 15/117* (2013.01); *A61K 31/711* (2013.01); *A61P 35/00* (2018.01); *C07K 16/2818* (2013.01); *C07K 16/2827* (2013.01)

(58) Field of Classification Search
CPC ............................ C12N 15/113; C12N 15/117
See application file for complete search history.

(56) References Cited

FOREIGN PATENT DOCUMENTS

WO    WO2016/057898 A1 *  4/2016  ........... C12N 15/117

\* cited by examiner

*Primary Examiner* — Amy H Bowman
(74) *Attorney, Agent, or Firm* — Muncy, Geissler, Olds & Lowe, P.C.

(57) ABSTRACT

The present invention discloses a combinational therapy for enhancing efficacy of immune checkpoint blockade for tumors with immune suppressive microenvironment. More specifically, this combination therapy involves the treatment of cancer through immune checkpoint inhibitors and CpG-oligodeoxynucleotides.

3 Claims, 13 Drawing Sheets

Specification includes a Sequence Listing.

SEQUENCE LISTING

<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: CpG-oligodeoxynucleotide
<220> FEATURE:
<221> NAME/KEY: misc_feature
<223> OTHER INFORMATION: n is a, c, g, or t
<220> FEATURE:
<221> NAME/KEY: misc_feature
<223> OTHER INFORMATION: n is a, c, g, or t.
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 1
gngggtcaac gttgagngng ngngng                                           26

<210> SEQ ID NO 2
<211> LENGTH: 26
<212> TYPE: DNA
<213> ORGANISM: Artificial Sequence
<220> FEATURE:
<223> OTHER INFORMATION: CpG-oligodeoxynucleotide
<220> FEATURE:
<221> NAME/KEY: misc_feature
<223> OTHER INFORMATION: n is a, c, g, or t.
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t -continued

<400> SEQUENCE: 2
gnggggacga tcgtcgngng ngngng                                              26

<210> SEQ ID NO 3
<211> LENGTH: 39
<212> TYPE: DNA
<213> ORGANISM: Artificial Sequence
<220> FEATURE:
<223> OTHER INFORMATION: CpG-oligodeoxynucleotide
<220> FEATURE:
<221> NAME/KEY: misc_feature
<223> OTHER INFORMATION: n is a, c, g, or t.
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t

```
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 3
tncncnantn gnancngntn tncncntngn ancngntnt                            39

<210> SEQ ID NO 4
<211> LENGTH: 47
<212> TYPE: DNA
<213> ORGANISM: Artificial Sequence
<220> FEATURE:
<223> OTHER INFORMATION: CpG-oligodeoxynucleotide
<220> FEATURE:
<221> NAME/KEY: misc_feature
<223> OTHER INFORMATION: n is a, c, g, or t.
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
```

```
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t

<400> SEQUENCE: 4
tncngntncn gntntntntn gntncngntn tntntngntn cngntnt                     47

<210> SEQ ID NO 5
<211> LENGTH: 37
<212> TYPE: DNA
<213> ORGANISM: Artificial Sequence
<220> FEATURE:
<223> OTHER INFORMATION: CpG-oligodeoxynucleotide
<220> FEATURE:
<221> NAME/KEY: misc_feature
<223> OTHER INFORMATION: n is a, c, g, or t.
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
```

-continued

```
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t

<400> SEQUENCE: 5
gntntngntn cngntntntn tntntngntn cngntnt                                37

<210> SEQ ID NO 6
<211> LENGTH: 49
<212> TYPE: DNA
<213> ORGANISM: Artificial Sequence
<220> FEATURE:
<223> OTHER INFORMATION: CpG-oligodeoxynucleotide
<220> FEATURE:
<221> NAME/KEY: misc_feature
<223> OTHER INFORMATION: n is a, c, g, or t.
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
```

-continued

```
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
```

```
<220> FEATURE:
<221> NAME/KEY: misc_feature
<222> LOCATION: (48)..(48)
<223> OTHER INFORMATION: n is a, c, g, or t

<400> SEQUENCE: 6
tncngntncn gntncngntn tncngnanan cngnancngn tntngnant            49
```

US 11,898,147 B2

CPG-OLIGODEOXYNUCLEOTIDE COMPOUNDS IN COMBINATION WITH IMMUNE MODULATORS FOR CANCER IMMUNOTHERAPY

BACKGROUND OF THE INVENTION

Technical Field of the Invention

The present invention relates generally to the field of cancer treatment, particularly to a cancer immunotherapy.

Background

PD-1 is one of best investigated immune checkpoint regulators that play important roles in maintaining homeostasis of the immune system for preventing disorders caused by over-activation of immune responses. PD-1 controls the late immune response of T cells in peripheral tissues, as its ligands are mainly expressed in nonlymphoid tissues. A variety of PD-1/PD-L1 monoclonal antibodies have been developed for anti-tumors by immune checkpoint blockade. Six PD-1 or PD-L1 antibodies have been approved by the US FDA for immunotherapy of different cancer types. Cancer therapy with these immune checkpoint inhibitors were demonstrated to have notable efficacy, nevertheless the response rate of patients with solid tumors is generally less than 30%.

CpG-oligodeoxynucleotides (CpG-ODNs) are synthetic activator of toll-like receptor 9 (TLR9) and TLR21 in different species. Mammals express TLR9 but lack of TLR21. The activation of mammalian TLR9 by CpG-ODNs induces immune responses including an innate immune response elicited within hours after CpG-ODN stimulation followed by a second phase of adaptive immune response occurred several days later.

Because of the activated immune response facilitates eradiation of cancer cells from body, the anti-tumor effect of CpG-ODN was investigated and has been demonstrated in various cancer animal models. In addition, CpG-ODNs are being investigated in clinical trials as therapeutic agent for cancer treatments, but so far none CpG-ODN has yet been approved for cancer therapy.

SUMMARY OF THE INVENTION

Accordingly, one aspect of the invention relates to a method for treating cancer, comprising administering an immune checkpoint blockade and an adjuvant composition to a patient in need thereof; wherein the adjuvant composition comprises at least one CpG-oligodeoxynucleotide.

In some embodiments, the said immune checkpoint blockade is selected from the group consisting of anti-PDI1, anti-PD-L1, and anti-CTLA4 antibody.

In some preferred embodiments, the said CpG-oligodeoxynucleotide is selected from the group consisting of CpG-1585 (SEQ ID NO:1), CpG-2216 (SEQ ID NO:2), CpG-1826 (SEQ ID NO:3), CpG-2006 (SEQ ID NO:4), CpG-2722 (SEQ ID NO:5), and CpG-M362 (SEQ ID NO:6).

In some embodiments, the said cancer possesses resistance to immunotherapy.

In some embodiments, the said cancer is selected from the group consisting of melanoma, non-small cell lung cancer, renal cell carcinoma, hodgkin lymphoma, head and neck cancer, urothelial carcinoma, hepatocellular carcinoma, and small cell lung cancer.

A further aspect of the invention relates to a pharmaceutical composition for treating cancer, comprising an immune checkpoint blockade and an adjuvant composition; wherein the adjuvant composition comprises at least one CpG-oligodeoxynucleotide.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Data represent mean±SEM (n=3 independent experiments). Asterisk *, , and * represent statistically significant difference $p<0.05$, $p<0.01$, and $<0.001$, respectively, compare to control or as indicated.

Human peripheral blood mononuclear cells (PBMCs) were treated with 0.5 μM CpG-ODNs as indicated. (A) After 4 h, cells were lysed and relative mRNA levels of different cytokines were determined by RT-qPCR. Expression level of β-actin was used as loading control. (B) After 24 h, cytokines as indicated secreted into cell culture medium were measured with ELISA.

Figure 2A:
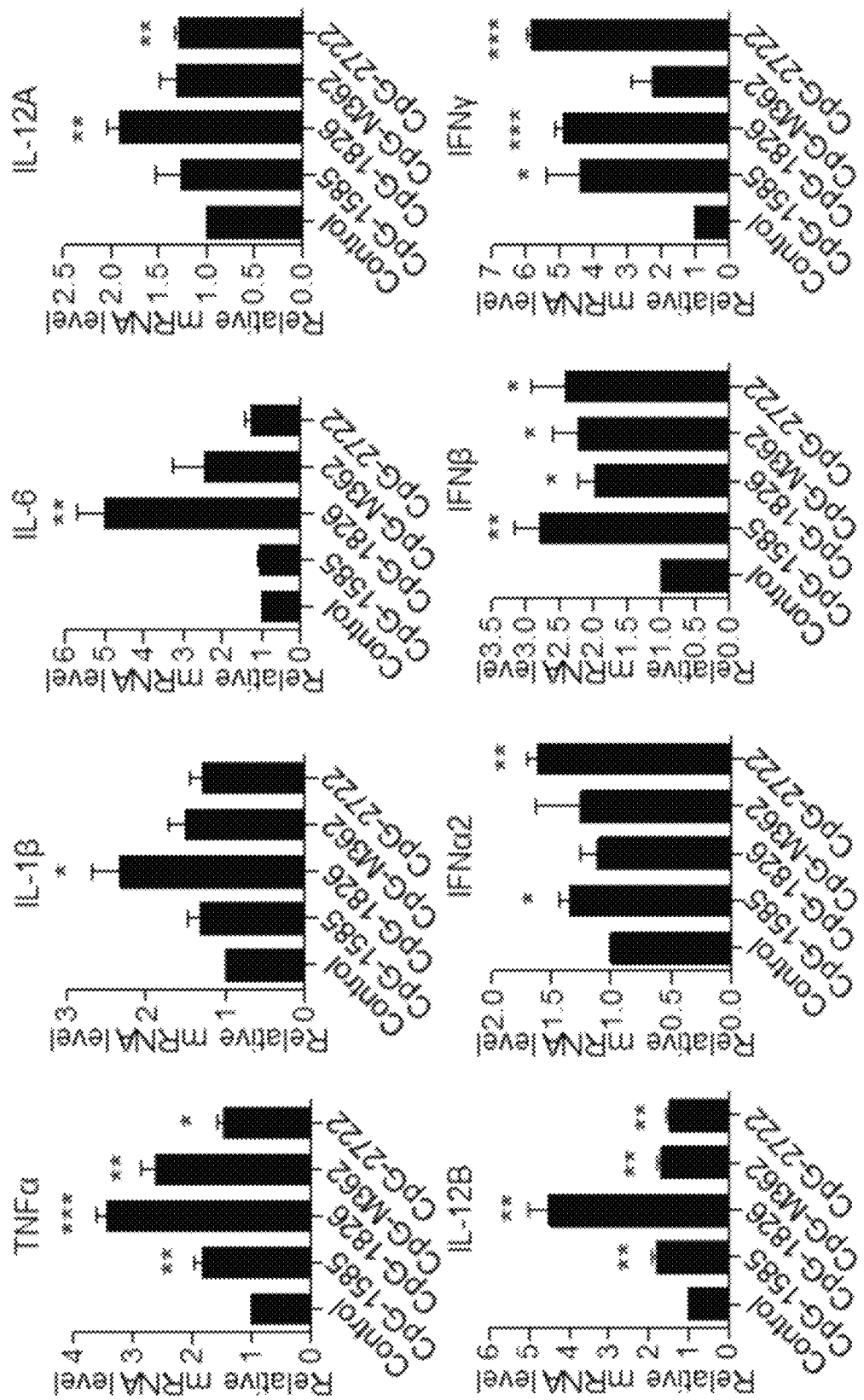
Figure 2B:
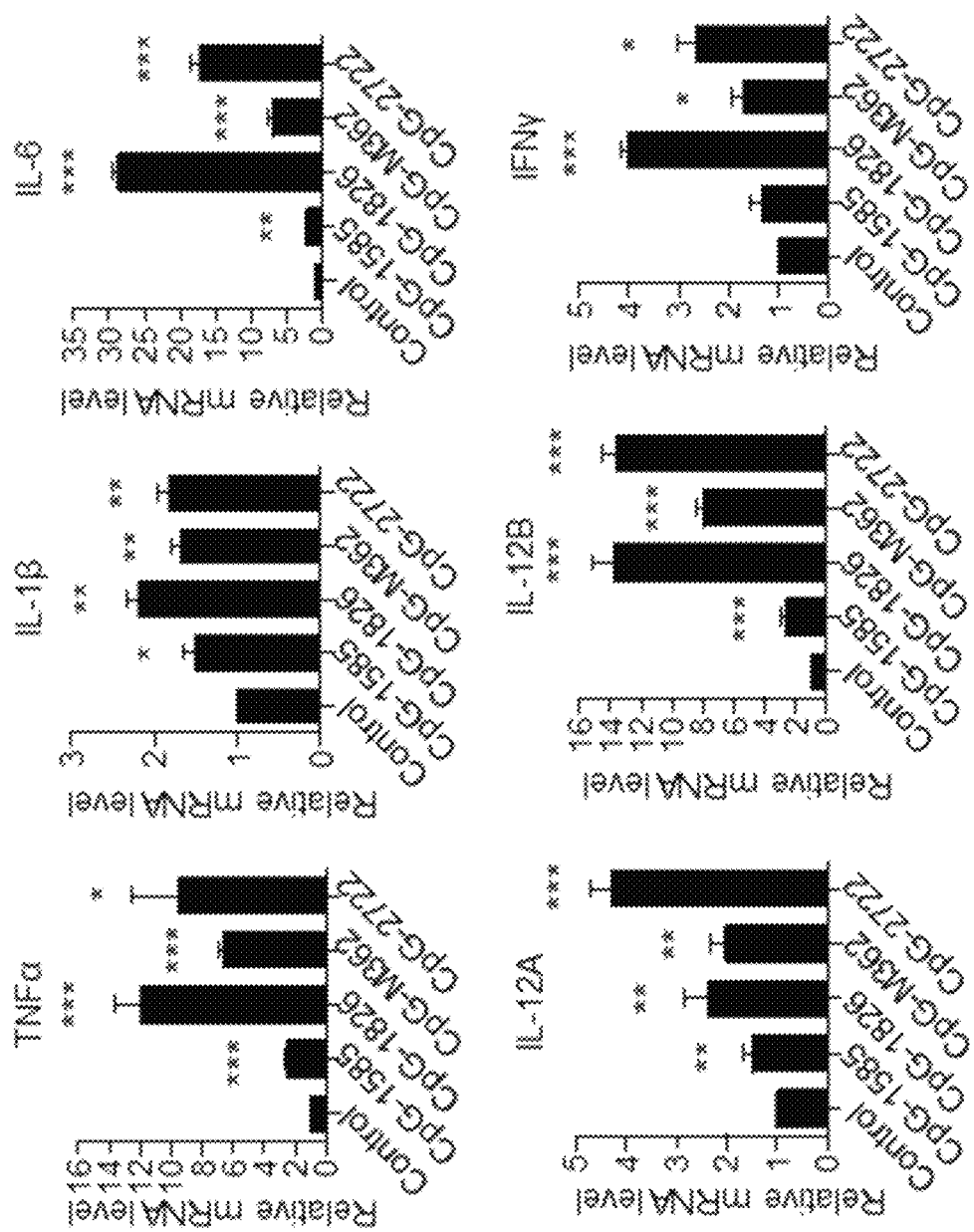

FIGS. 2A and 2B. Cytokine inducing effect of CpG-2722 in mouse cells (A) Mouse bone marrow-derived macrophages BMDMs) and (B) mouse splenocytes were treated with 0.5 μM of different CpG-ODNs as indicated for 4 h. Relative mRNA level of cytokines were analyzed by RT-qPCR. Expression level of β-actin was used as loading control.

Figure 3:
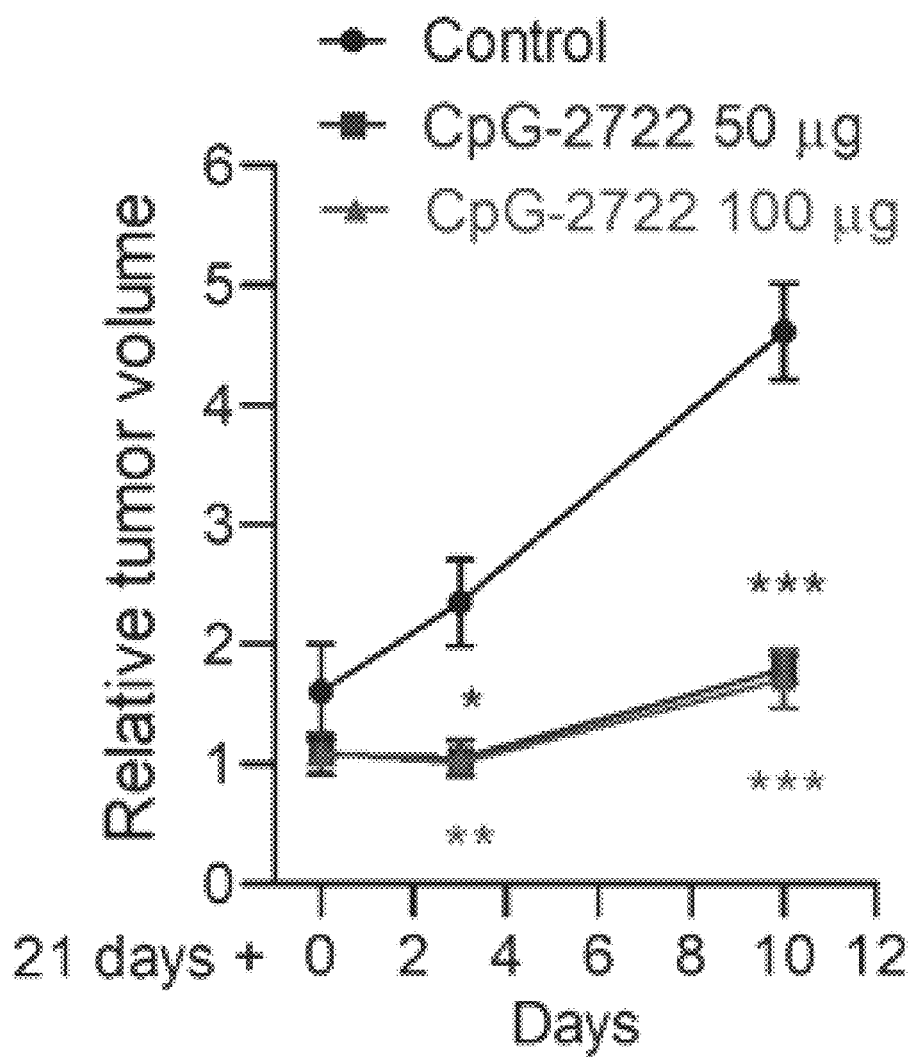

FIG. 3. Suppressing effect of CpG-2722 on growth of tumor cell

C57BL/6J mice were orthotopically injected with $2\times10^6$ NHRI-HNC1 cells to establish HNSCC. Twenty-one days later when the tumors reached to 250-550 mm³, the mice were intratumorally injected with control vehicle, 50 μg, or 100 μg CpG-2722 twice/week. Tumor size was measured at the 21st, 24th, and 31st days (each group contains 3 mice and three tumors).

FIGS. 4A-4E. CpG-2722 augments the suppressing effect of immune checkpoint inhibitor on growth of tumor cell.

(A) C57BL/6J mice were orthotopically injected with $2\times10^6$ NHRI-HNC1 cells to establish HNSCC. Nine day later when the tumors reached to around 100 mm³, the mice were intratumorally injected with control vehicle or 50 μg CpG-2722 every three days in combination with or without intraperitoneal injected 10 μg anti-PD-1 antibody once per week for two weeks as illustrated. (B) Tumor sizes were measured every three day (each group contains 5 mice and 5 tumors). (C) Endpoint of the tumor growths represent as indicated. (D) Tumor samples were visualized by H&E staining (upper panel 40×). Immunohistochemistry staining was performed to determine CD8 cytotoxic T cell infiltrations (middle panel 20× and bottom panel 40×). Scale bar represents 100 μm. (E) CD8⁺ cells were quantified by using Image J software at 20× magnification filed.

Figure 5:
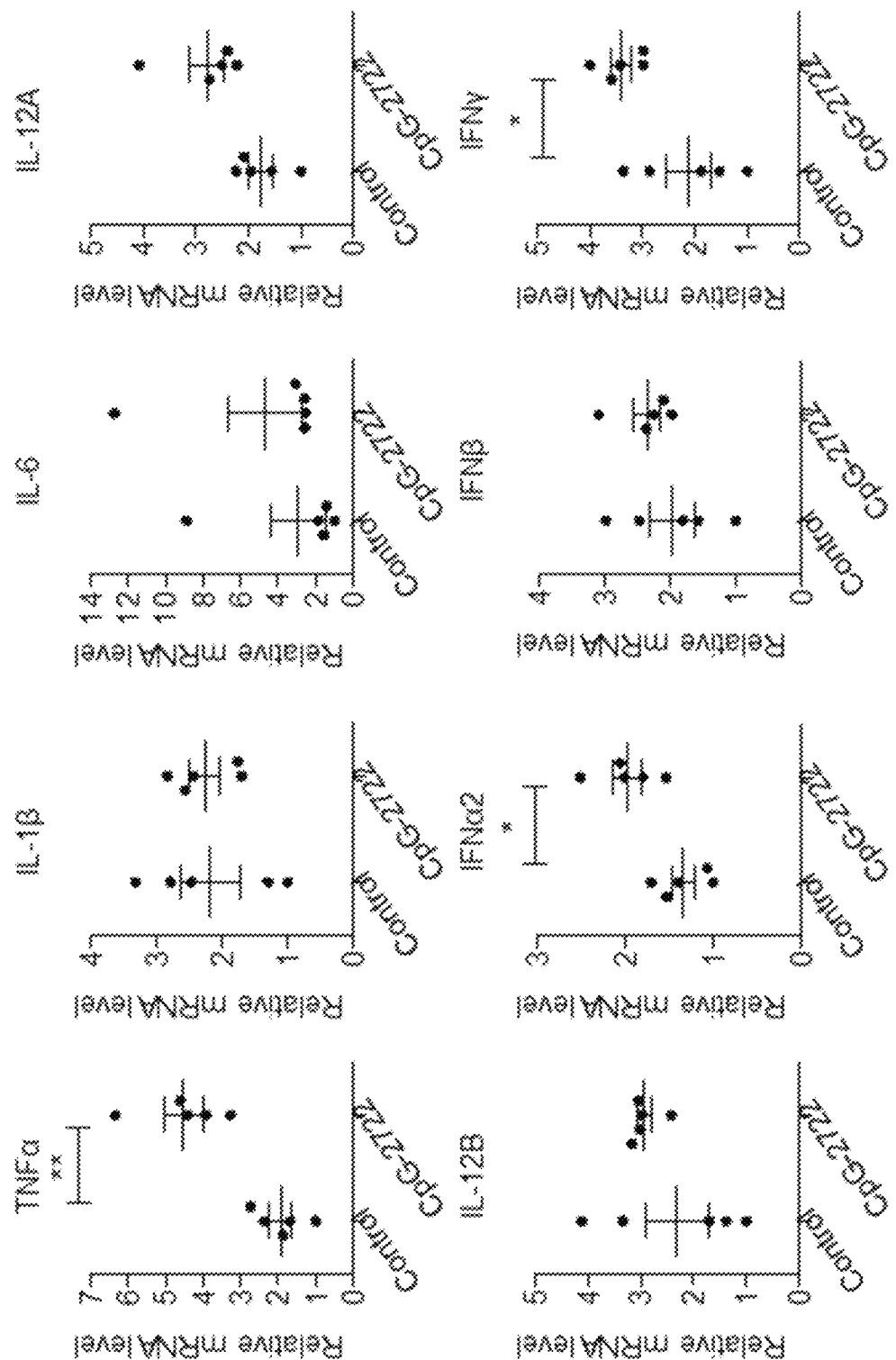

FIG. 5. Cytokine inducing effect of CpG-2722 in tumor cell

C57BL/6J mice were orthotopically injected with $2\times10^6$ NHRI-HN1 cells and HNSCCs were grew to around 100 mm³. These mice were intratumorally injected with control vehicle or 50 μg CpG-2722 and euthanized on the next day. Total RNA from tumor tissue samples were isolated by Trizol reagent, and mRNA expression levels of cytokines were determined by RT-qPCR. Expression level of β-actin was used as loading control.

Figure 6:
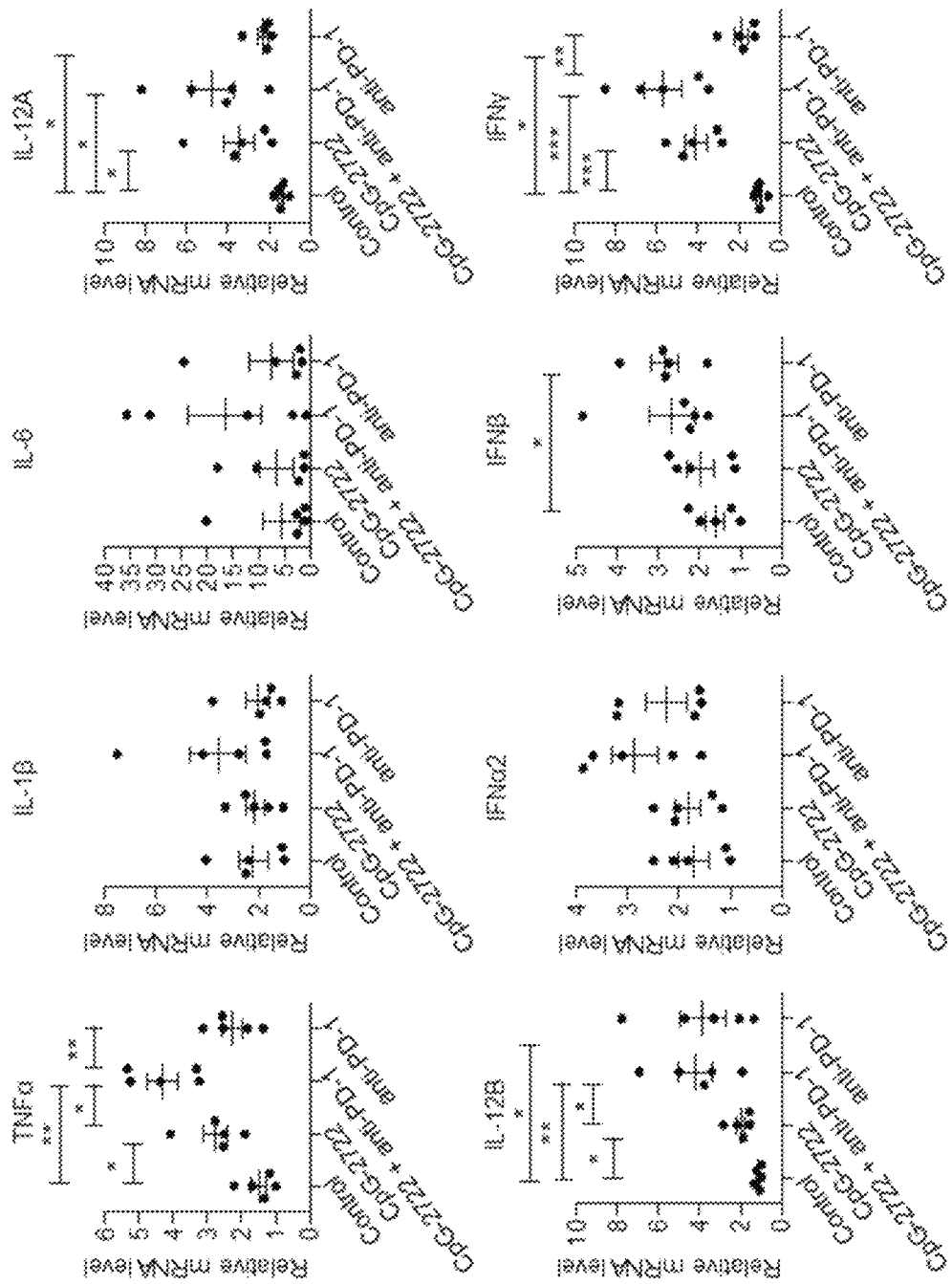

FIG. 6. CpG-2722 alone and in combination with immune checkpoint inhibitor augments cytokine genes expression in tumor cell Tumor bearing mice in the experiment for FIG. 4 were treated with CpG-2722 and anti-PD-1 alone or in combine for 15 days and euthanized for collection of tumor samples. Total RNAs from the tumors were isolated by Trizol reagent. The mRNA expression level of different cytokines was measured by RT-qPCR. Expression level of β-actin was used as loading control.

Figure 7A:
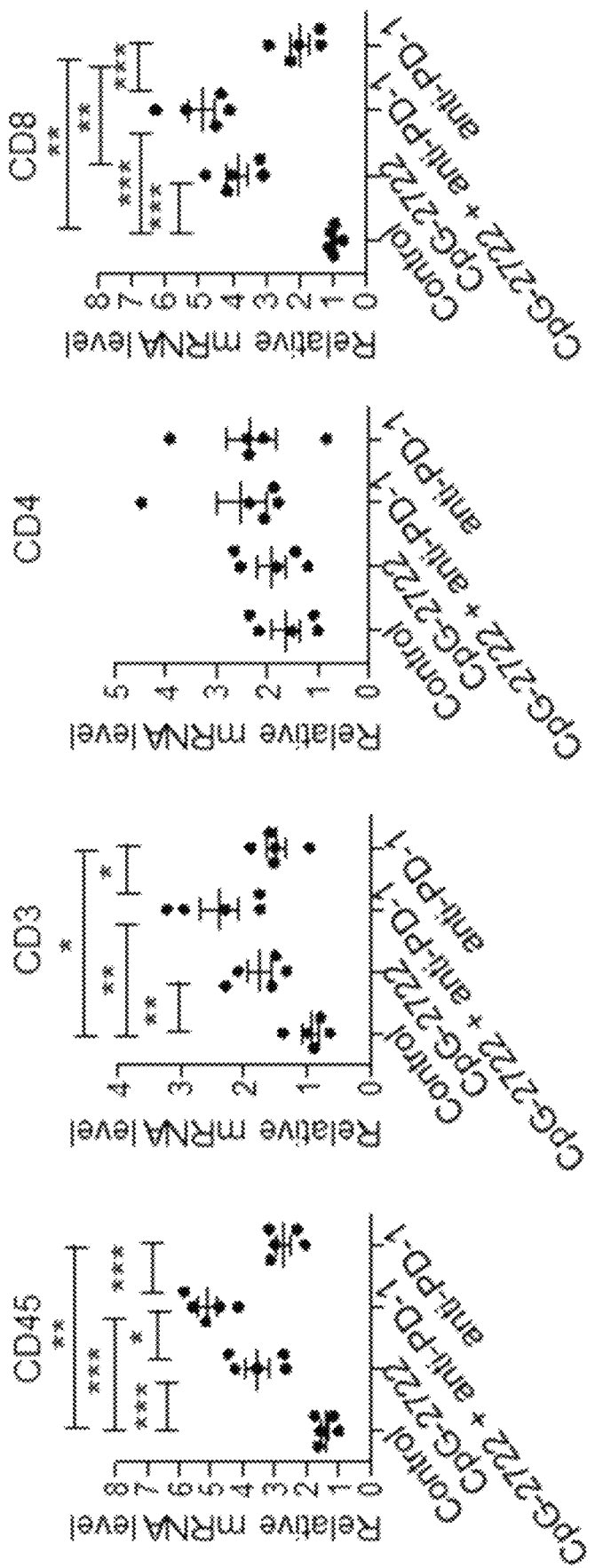
Figure 7B:
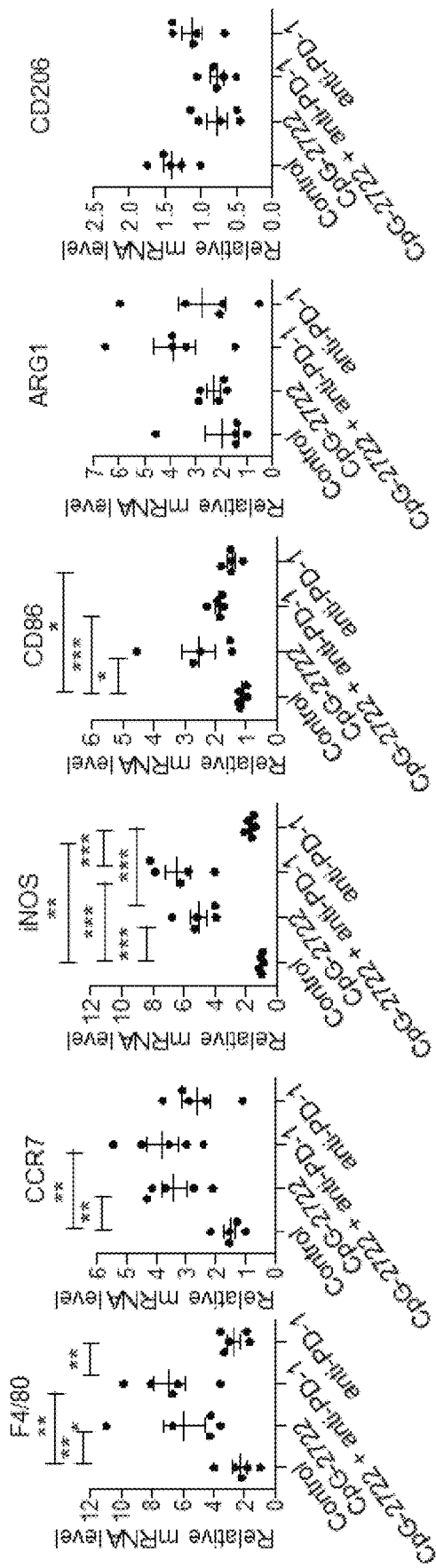

FIGS. 7A-7B. CpG-2722 alone and in combination with immune checkpoint inhibitor increase the accumulation of CD8 T cells and M1 macrophages in tumor cell. Tumor bearing mice in the experiment for FIG. 4 were treated with CpG-2722 and anti-PD-1 alone or in combine for 15 days and euthanized for collection of tumor samples. Total RNAs from the tumors were isolated by Trizol reagent. Expression of markers for (A) different types of T cells, and (B) different type of macrophages were analyzed by RT-qPCR. Expression level of β-actin was used as loading control.

DETAILED DESCRIPTION OF THE INVENTION

All technical and scientific terms used herein, unless specifically stated otherwise, have the same meaning as commonly understood by one of skill in the art. In the event of a conflict in meaning, this specification shall prevail.

Reagents, Antibodies and Human Peripheral Blood Mononuclear Cells (PBMCs) Cells

All CpG-ODNs were purchased from Integrated DNA Technologies, Inc. CpG-ODNs dissolved in DNase/RNase free water, and aliquots of CpG-ODNs were stored at −20° C. Anti-PD-1 antibody used for in vivo treatment were purchased from InvivoGen. (Cat. No. mpd1-mab15-10) Rat anti-mouse CD8 antibody used for immunohistochemistry were purchased from Invitrogen (Cat. No. 14-0808-82). Trizol reagent and SuperScript™ IV kit were purchased from Invitrogen. SYBR® Green PCR kit was purchased from Qiagen. Human PBMCs were purchased from ZenBio, Inc.

Mouse Splenocytes Preparation

Mouse splenocytes were isolated from 6 to 8-week-old C57BL/6J mouse (National Laboratory Animal Center, Taiwan). Briefly, mouse spleen was collected and pounded by using plunger of a syringe and aspirates the fragments onto a 40 μm nylon cell strainer (BD Falcon™) attached to a 50 ml conical tube. Single cells are squeezed out of spleen fragments, pass through cell strainer, and centrifugate at 1500 rpm for 5 min. Cell pellet resuspends with RBC lysis buffer for 2 min and subsequently terminates lysis reaction by adding 30 ml PBS. Splenocytes were centrifugated at 1500 rpm for 5 min and culture in RPMI 1640 completed medium at 37° C. in 5% $CO_2$ incubator.

Mouse Bone Marrow Derived Macrophages (BMDMs) Preparation

Mouse BMDMs were isolated from 6 to 8-week-old C57BL/6J mouse. Bone marrow cells were washed out of tibias and femurs by using a syringe with 27 G needle, pass through 40 μm nylon cell strainer attached to a 50 ml conical tube, and centrifugate at 1500 rpm for 5 min. Cell pellet resuspended with RBC lysis buffer for 2 min and immediately terminated lysis reaction by adding 30 ml PBS. Bone marrow cells were centrifugated at 1500 rpm for 5 min and cultured in 70% DMEM completed medium containing 10% FBS, L-glutamine, antibiotics, 10 mM HEPES buffer, and 30% L929 conditional medium at 37° C. in 5% $CO_2$ incubator for 7 days. Un-adherent cells were removed and BMDMs were harvested by gentle scraping. One million BMDMs were seeded onto 6 well plate for different CpG-ODNs stimulation following additional 3 days culture.

RNA Isolation

Total RNA from mouse splenocytes, BMDMs and human PBMCs was isolated with Illustra™ RNAspin Mini Kit (GE Healthcare) following manufacturer's protocol. RNA samples from NHRI-HN1 derived tumors were isolated by using TRIzol reagent.

Reverse Transcription-Quantitative PCR (RI-qPCR) Analysis

Cells were treated with different CpG-ODNs at 0.5 μM for 4 h RNA samples were then isolated and reverse transcription performed by using the SuperScript™ IV First-Strand Synthesis System (Invitrogen). We performed quantitative PCR by using QuantiNova™ SYBR® Green PCR Kit (Qiagen) and Applied Biosystems ViiA™ 7 Real-Time PCR System for gene expression analysis. The expression level of β-actin was used as loading control.

Enzyme-Linked Immunosorbent Assay for Cytokine Production

Human PBMCs were treated with or without different CpG-ODNs as indicated for 24 h and cell culture media were collected. Production of cytokines were measured using enzyme-linked immunosorbent assay (ELISA) kits from eBioscience (San Diego, CA, USA) following the manufacturer's protocol.

Syngeneic Orthotopic Cancer Animal Model

We subcutaneously injected indicated number of NHRI-HN1 cells with matrigel (BD Biosciences) into oral cavity of 4 to 6-week-old C57BL/6J mice to grow tumor. When tumors reached to indicated size, the mice were intratumorally injected with indicated amount of CpG-2722 twice/week, in combination with or without 10 μg anti-PD-1 antibody once/week. All groups contain 5 mice and 5 tumors. Tumor volume of mice bearing NHRI-HN1 derived tumor was measured by using the formula=length× $(width)^2 \times 0.5$.

Immunohistochemistry

Paraffin embedded NHRI-NH1 derived tumors were sectioned into 5 μm tissue slides. These tissue slides were rehydrated from graded concentrations of ethanol to PBS, and blocked endogenous peroxidase with 3% hydrogen peroxide for 5 min. For CD8 staining, a rat monoclonal antibody against mouse CD8 was used at dilution of 1:50 and incubated at room temperature for 1 h. The detection was processed in the Discovery XT automated IHC/ISH slide staining system (Ventana Medical System, Inc. Tucson), using ultraView Universal DAB Detection Kit (Ventana Medical System, Inc. Tucson), according to the manufacturer's instruction. Immunostaining was visualized after counterstaining with hematoxylin.

The species-specific activity of a CpG-ODN is determined by its nucleotide sequence and the length. For example, CpG-2006 is more potent in activating human cells than is CpG-1826, in contrast CpG-1826 is more potent in activating murine cells than is CpG-2006. As shown in Table 1, the CpG-2006 contains 24 nucleotides and three copies of the GTCGTT-hexamer motif. CpG-1826 contains 20 nucleotides and two copies of the GACGTT-hexamer motif.

CpG-2722 contains 19 nucleotides with two copies of GTCGTT-hexamer motif and four thymidines between these two hexamer motifs. This CpG-ODN was previously developed for activation of grouper (*Epinephelus* spp.) TLR21s and also displayed activities on mouse TLR9 and human TLR9, thus is an universal CpG-ODN for multiple species. To explore its usages as an immunostimulant in mammals, in this study we first compared its cytokine induction profiles in parallel with different type of CpG-ODNs. Of them, same as the CpG-2722, CpG-2006 is a type B CpG-ODN containing a phosphorothiolate backbone throughout the entire sequence with three CpG-motifs. CpG-2216 is a type A CpG-ODN with preferential activity to human cells and contains a central phosphodiester palindrome region with one CpG-motifs in the palindrome and poly (G) sequences with a phosphorothioate backbone attached to the 5' and 3' ends. CpG-M362 is a type C CpG-ODN with activities for both of human and mouse cells. This CpG-ODN contains phosphorothioate backbone with one or two CpG-motifs and a palindromic sequence at the 3' end (Table 1).

Example 2

Induction of Cytokine Expressions in Mouse Cells by CpG-2722

The immunostimulatory activities of CpG-2722 in mouse cells compared to other type of CpG-ODNs were further investigated. In this disclosure, a type A CpG-1585 and a type B CpG-1826 with nucleotide sequence designed for activation of mouse cells (Table 1) were used to replace the CpG-2216 and CpG-2006 used in the studies with human cells. Mouse bone marrow derived macrophages (BMDMs) were treated with these CpG-ODNs and induction of different gene expressions were analyzed with RT-qPCR. In these cells, the CpG-1826 had better activities in inducing expression of inflammatory cytokines including TNF-α, IL-1β, and IL-6 and IL-12B than other CpG-ODNs. In contrast, the CpG-2722 had similar activities as this CpG-1826 in induction expression of IL-12A and IFN-γ. Further, CpG-2722 activated the expression of IFN-α2 and IFN-β as a type A CpG-ODN (FIG. 2A). In addition to these, isolated mouse splenocytes were stimulated with these CpG-ODNs and

TABLE 1

Structural features of CpG-ODNs used in this study

| Name | Type | Species-perference | Sequence |
|---|---|---|---|
| CpG-1585 | A | Mouse | G*GGGTCAACGTTGAG*G*G*G*G*G |
| CpG-2216 | A | Human | G*GGGGACGATCGTCG*G*G*G*G*G |
| CpG-1826 | B | Mouse | T*C*C*A*T*G*A*C*G*T*T*C*C*T*G*A*C*G*T*T |
| CpG-2006 | B | Human | T*C*G*T*C*G*T*T*T*T*G*T*C*G*T*T*T*T*G*T*C*G*T*T |
| CpG-2722 | B | Mouse/Human/Fish | G*T*T*G*T*C*G*T*T*T*T*T*T*G*T*C*G*T*T |
| CpG-M362 | C | Mouse/Human | T*C*G*T*C*G*T*C*G*T*T*C*G*A*A*C*G*A*C*G*T*T*G*A*T |

EXAMPLES

Example 1

Induction of Cytokine Expressions in Human Cells by CpG-2722

Figure 1A:
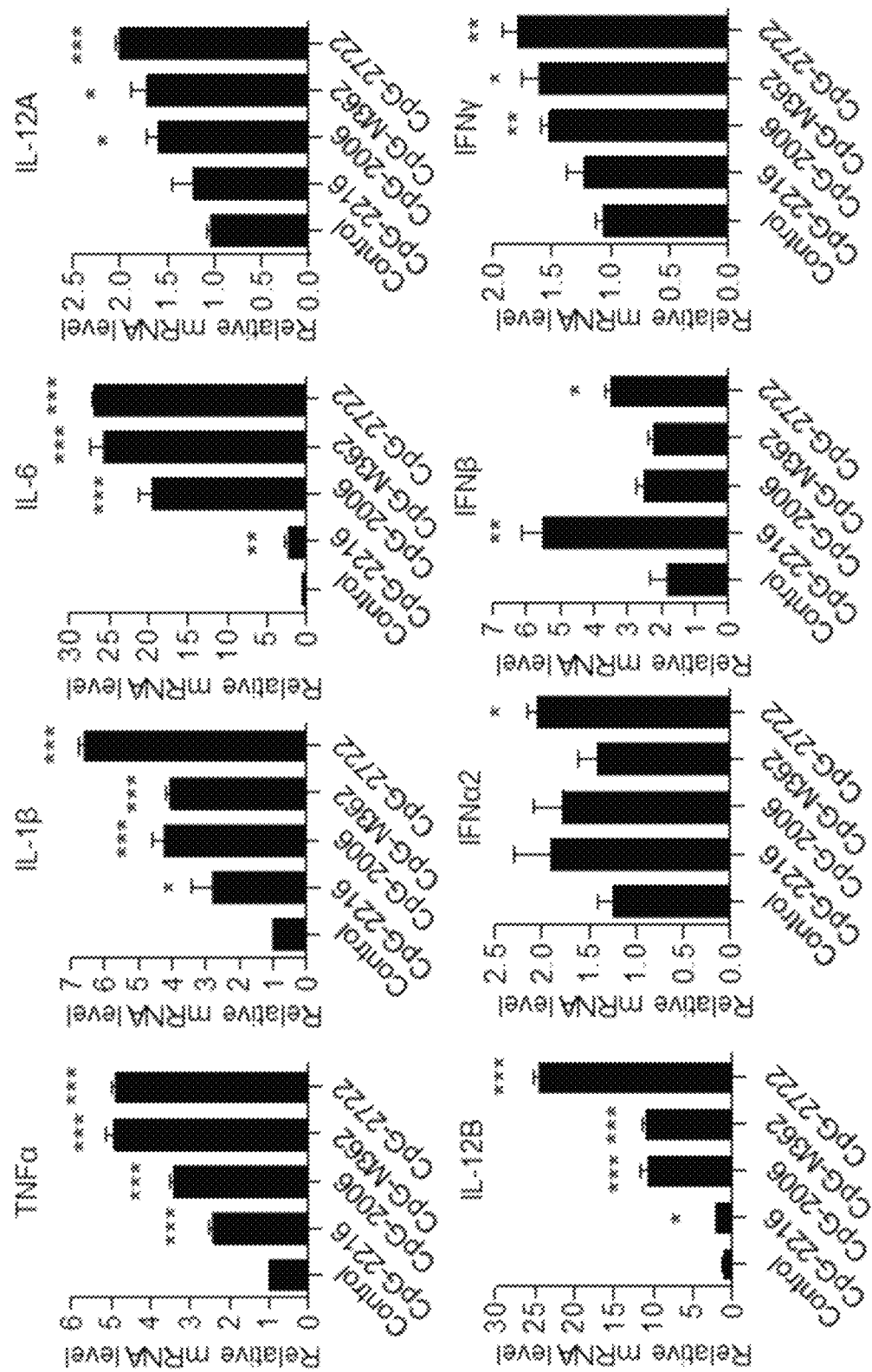
FIGS. 1A and 1B. Cytokine inducing effect of CpG-2722 in human cells
Figure 1B:
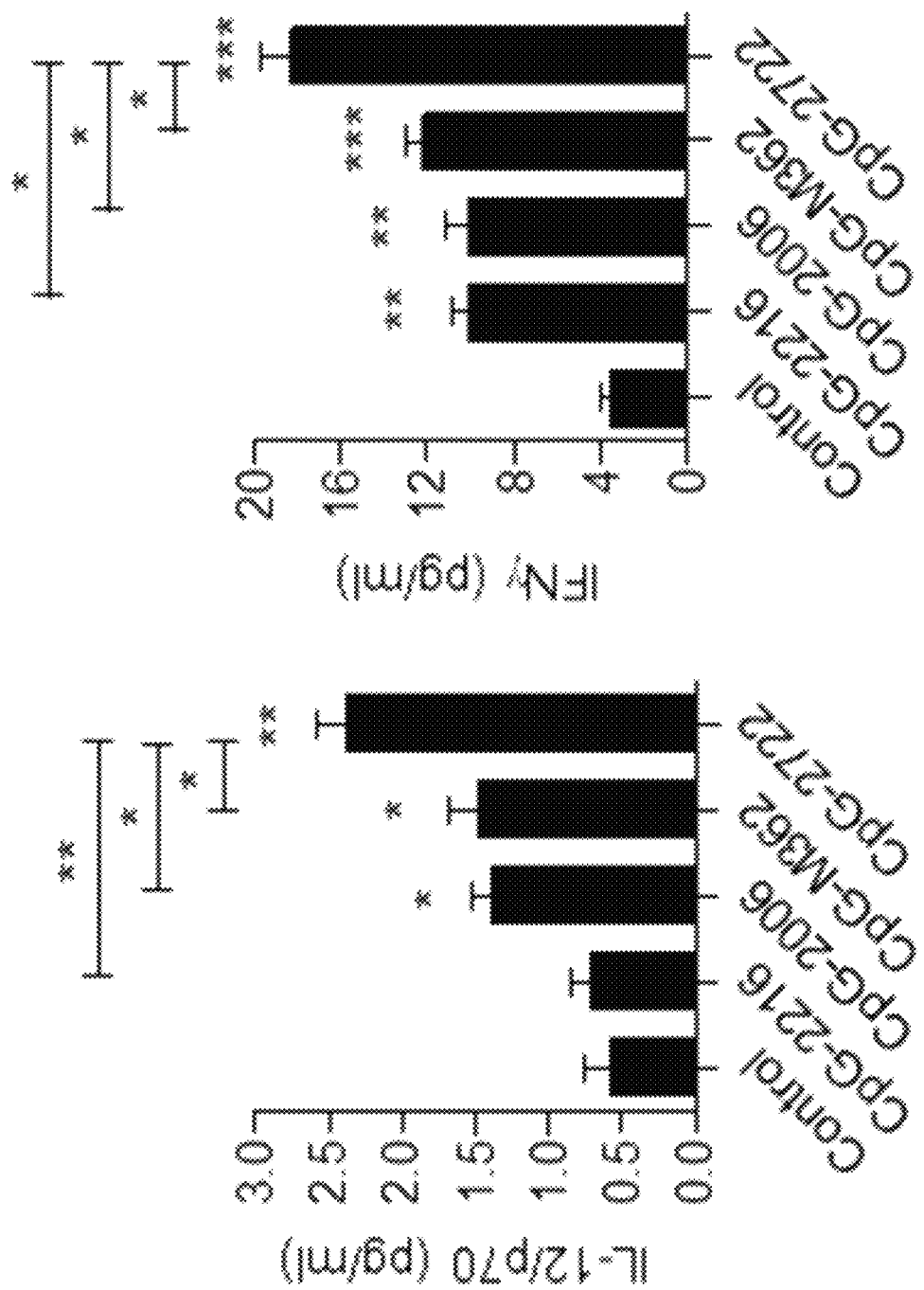

Human peripheral blood mononuclear cells (PBMCs) were stimulated with these CpG-ODNs and expression of different cytokine genes were analyzed with reverse transcription-quantitative polymerase chain reaction (RT-qPCR). The results revealed that CpG-2722 exhibited activities to induce expression of inflammatory cytokines including TNF-α, IL-1β, IL-6, IL-12B, and IFN-γ as the CpG-2006 and the CpG-M362 nevertheless it also activated expression of type I IFNs including IFNα2 and IFN-β like a type A CpG-ODN (FIG. 1A). IL-12p70 is a heterodimer of IL-12A and IL-12B. This cytokine and the IFN-γ play key role in promoting T cell proliferation and activation for antitumor responses. Therefore, the production of these two cytokines in cell culture medium were verified with ELISA assay. Consistent with its ability of inducing cytokine expressions, the CpG-2722 showed good activities on induction of IL-12 and IFN-γ productions than other CpG-ODNs (FIG. 1B).

gene expression of different cytokines were analyzed. In general, CpG-2722 and CpG-1826, the two type B CpG-ODNs had better activities to induce expression of these inflammatory cytokines including the IL-12A, IL-12B, and IFN-γ compared to the type A and type C CpG-ODNs tested (FIG. 2B).

Example 3

Antitumor Activity of CpG-2722

CpG-2722 are capable of inducing expression of inflammatory cytokines IL-12 and IFN-γ as type B CpG-ODNs and inducing type I interferons as type A CpG-ODNs in both human and mouse cells (FIGS. 1A, 1B, 2A and 2B). These cytokines, play critical role in boosting immune responses for eradication of cancer cells. A cancer cell line, NHRI-NH1 established from C56BL/6J derived oral squamous cell carcinoma cells was used for studying cancer immunobiology. These NHRI-NH1 cells ($2\times10^6$ cell/mouse) were syngeneic injected into the buccal mucosa of mice to develop orthotopic tumors. Twenty-one days later, when the size of tumors reached 250-550 mm$^3$, these mice were intratumorally injected with 50 μg or 100 μg of CpG-2722 every 3 days for 3 times and tumor growth was monitored. The results showed that CpG-2722 had similar effectiveness on inhibition of the tumor growth at both doses (FIG. 3). Therefore, the dose of 50 μg CpG-2722 per mouse was used in following examples.

Example 4

Cooperative Effect of Combining CpG-2722 and Anti-PD-1 on Suppression of Tumor Growth While nivolumab and pembrolizumab have been approved for patients with head and neck cancers, only less than 20% of the patients respond to the immune checkpoint inhibitors. Therefore, there is need to improve the efficacy for this therapy with immune checkpoint blockade. The effect of combining CpG-2722 and anti-PD-1 on suppression of tumor growth was investigated with the NHRI-NH1 syngeneic orthotopic cancer animal model.

Figure 4A:
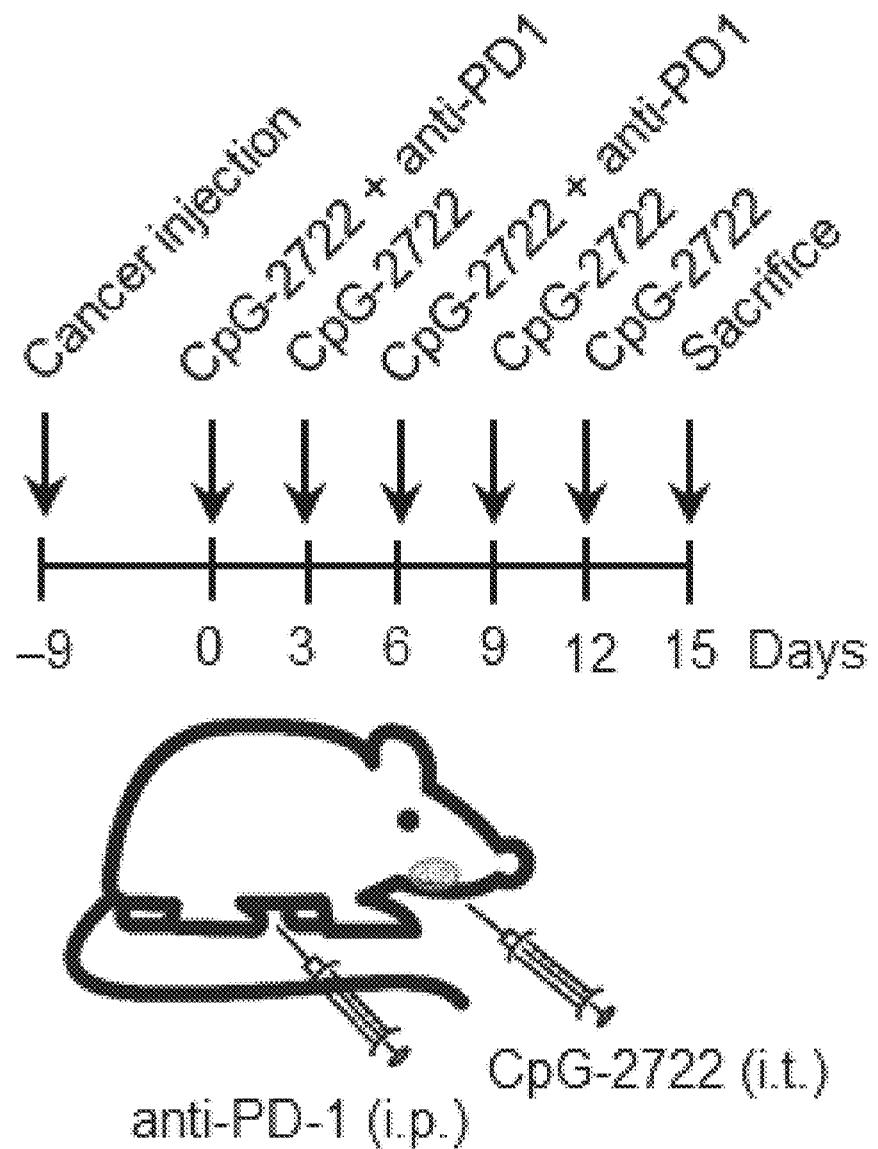
Figure 4B:
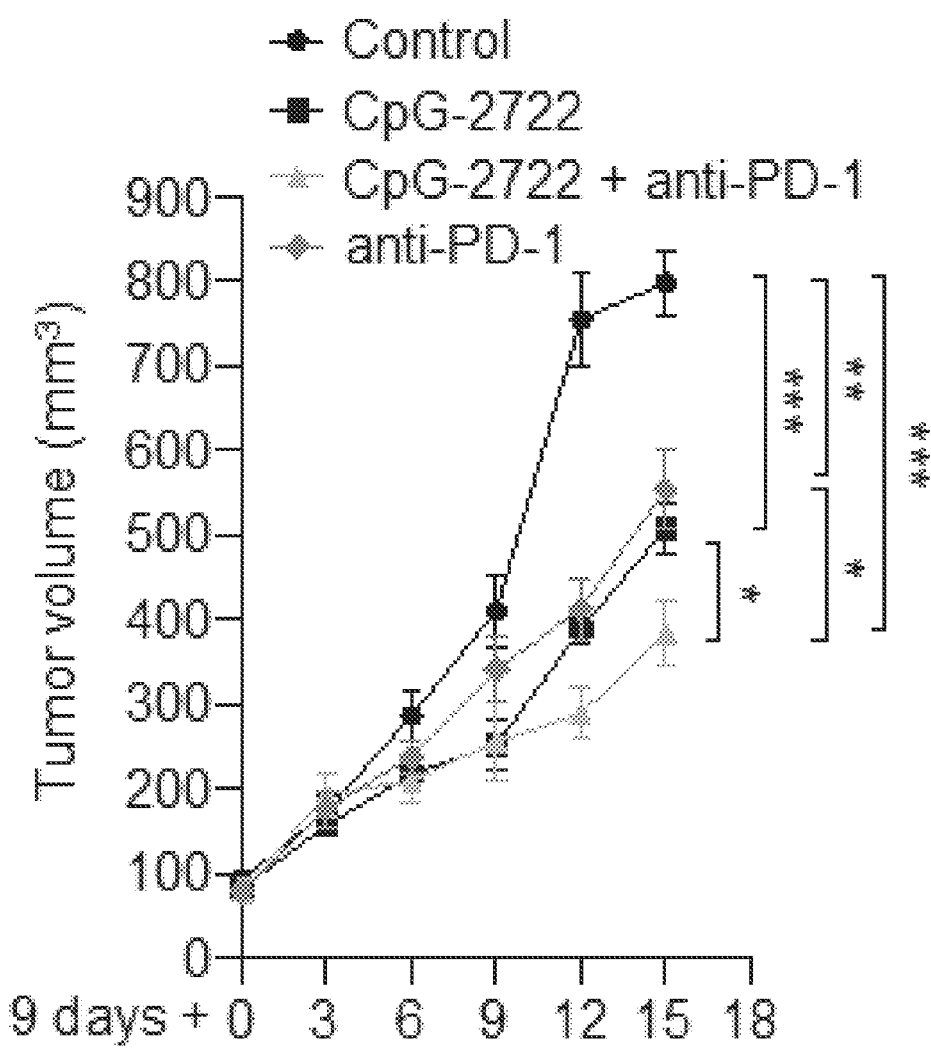
Figure 4C:
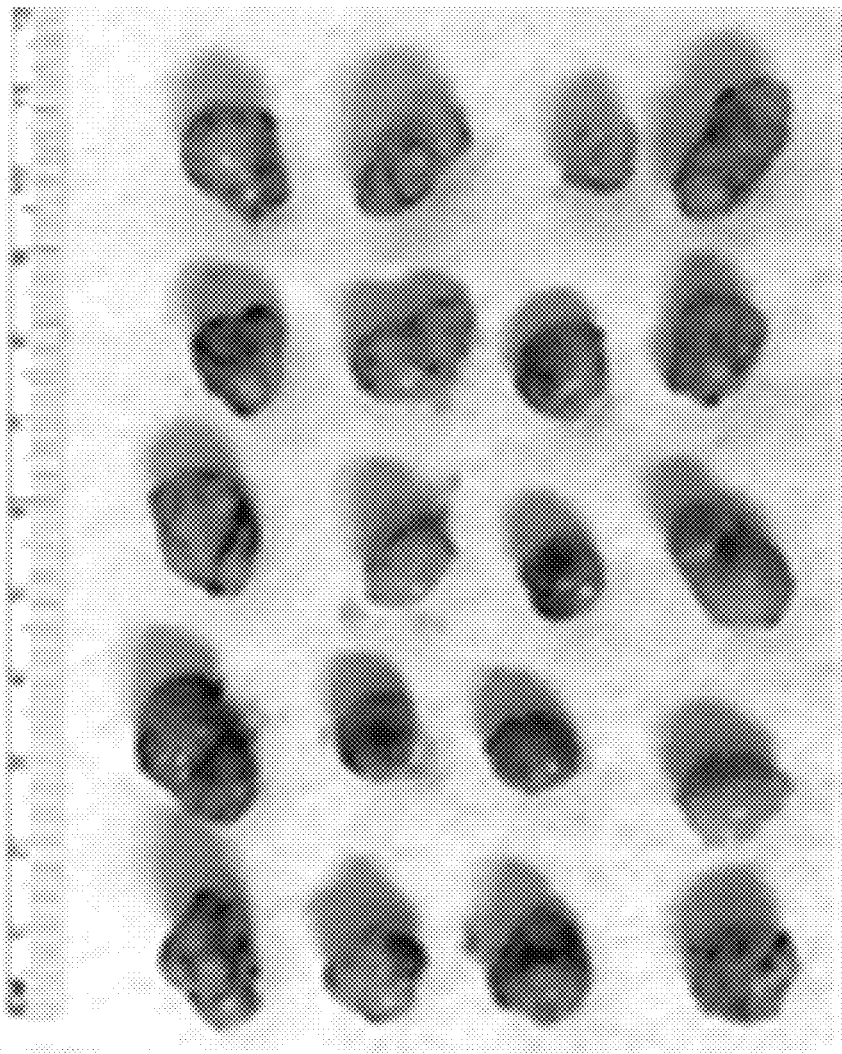
Figure 4D:
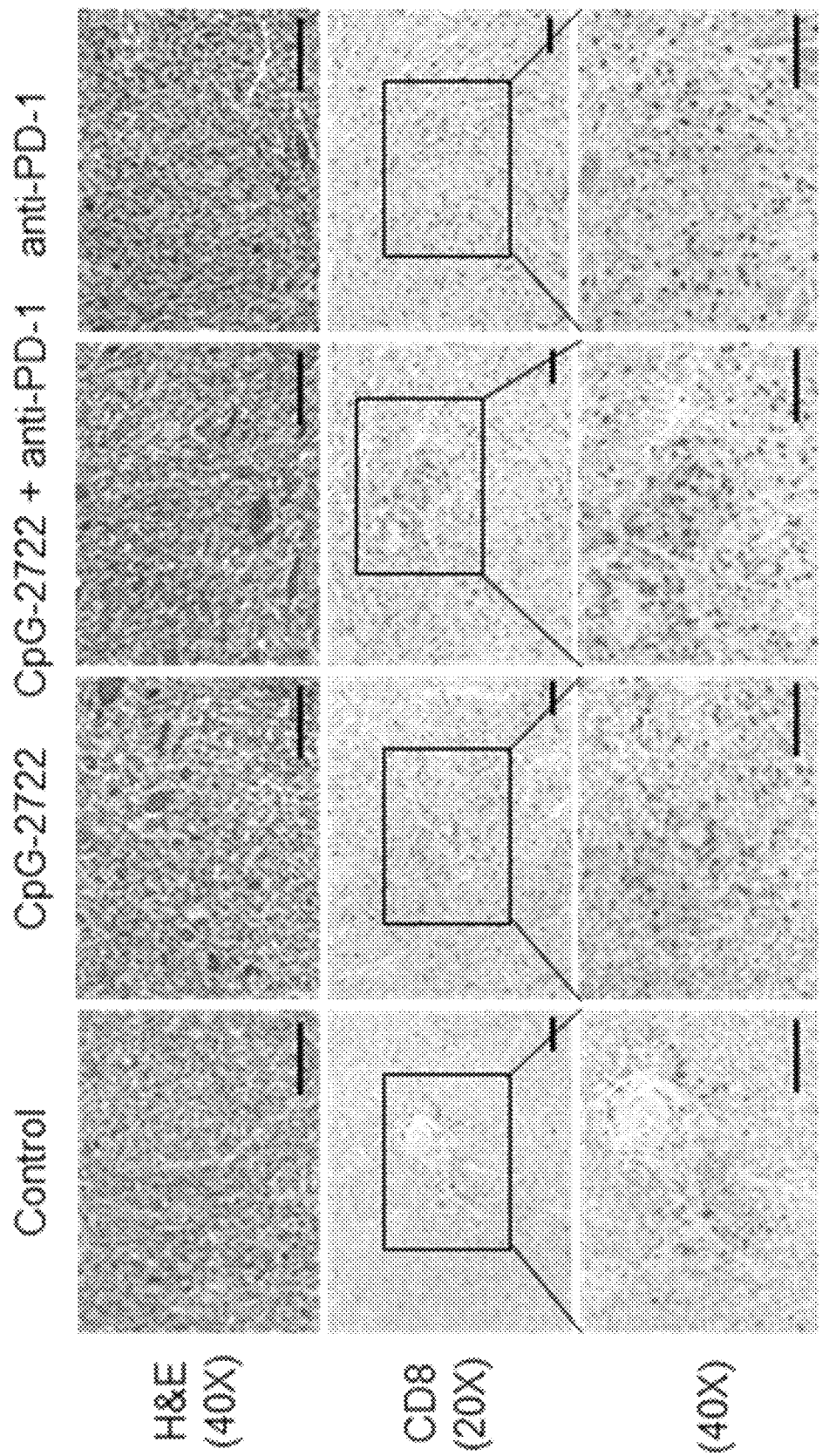

Two sets of studies were performed. In the first set of experiments, tumors were growth for 9 days to about 100 mm$^3$, the mice were then continuously intratumorally injected with CpG-2722 every 3 days and intraperitoneally injected with anti-PD-1 at day 0 and day 6 after the injection of CpG-2722 (FIG. 4A). These mice were monitored for the tumor growths. Administration of CpG-2722 and anti-PD-1 alone suppressed tumor growth. Combination of CpG-2722 and anti-PD-1 showed a more effective suppression on tumor growth than administration with these two agents alone (FIG. 4B). The mice were euthanized at day 15 after the treatment of the CpG-2722 and anti-PD-1 and tumors were taken for analysis of their sizes (FIG. 4C). Further histochemical analysis of the tumor tissues revealed that both CpG-2722 and anti-PD-1 treatments increased the infiltration of CD8$^+$ T cells in the tumors and combination of CpG-2722 and anti-PD-1 further increased the CD8$^+$ T cells infiltration (FIG. 4D).

In the second set of study, the experiments were performed similar to those in the first set, except that the injection of CpG-2722 was changed from every three days to every four days, and route and schedule for administration of anti-PD-1 was substituted by intravenous injection at day 8 and day 16 following the administration of the CpG-2722. The results also showed a cooperative effect of CpG-2722 with anti-PD-1 on suppression of tumor growth. Further like that in the first set of study, there is a correlation between extents of CD8 T cells accumulation in the tumors and the therapeutic effects of the CpG-2722 and/or anti-PD-1 treatments on suppression of tumor growth.

Example 5

Activate Immune Responses in Tumor Microenvironment by CpG-2722

Mechanism by which antitumor effect was increased by the combination of CpG-2722 and anti-PD-1 was further investigated. To study cytokine expressions and their kinetics in the CpG-2722 treated tumors, mice were injected with the NHRI-NH1 cells to establish head and neck cancers. When the tumors reached to about 100 mm$^3$, the mice were intratumorally injected with CpG-2722 and euthanized 24 hours later. Analysis for cytokine expression profiles in the tumors by RT-qPCR revealed that expression of TNF-α, IFNα2 and IFN-γ genes were induced at the second day after intratumoral injection of the CpG-2722 while the induction of other cytokines was not significant (FIG. 5). Further, the tumors from the control, CpG-2722, anti-PD-1 and CpG-2722 plus anti-PD-1 15 days continuously treated mice in the experiment of FIGS. 4A-4E were analyzed with RT-qPCR for the cytokine expression profiles in the tumors. Gene expression of TNF-α, IL-12A, IL-12B, IFN-β and IFN-γ were significantly increased in the tumors derived from CpG-2722 and CpG-2722 plus anti-PD-1 treated mice (FIG. 6). The capability of CpG-2722 to induce expression of these cytokines in tumors are consistent with its ability to induce expression of these cytokines in immune cells (FIGS. 1A, 1B, 2A, and 2B). In addition, the profiles of cytokine inductions in tumors at the second day after CpG-2722 injection and at 15 days after the continuous injection of CpG-2722 (FIGS. 5 and 6) revealed that multiple injections of CpG-ODN are required to achieve an effective induction of cytokines in the tumors.

The accumulation of immune cells in the tumors from the CpG-2722 and anti-PD-1 treated mice were further investigated with RT-qPCR analysis of different cell makers. The results showed an increase of CD3 and CD8 positive T cells in the tumors from CpG-2722 and CpG-2722 plus anti-PD-1 treated mice (FIG. 7A). Macrophages is a large population of leukocyte in tumor microenvironment. These tumors associated macrophages usually can be polarized into two subsets, inflammatory M1 macrophages and anti-inflammatory M2 macrophages. Analysis of marker including F4/80 for macrophages, CCR7, iNOS, and CD86 for M1 macrophages, and ARG1, CD206 for M2 macrophages revealed CpG-2722 and CpG-2722 plus anti-PD-1 enhanced the accumulation of macrophages in tumors. In addition, M1 but not M2 macrophages were accumulated in parallel with the increased macrophages (FIG. 7B). In summary, these results indicate that CpG-2722 is capable of sharpening up tumor microenvironment by inducing key antitumor cytokines including IL-12, IFN-γ and type I IFNs, and increasing the accumulation of inflammatory M1 macrophages and CD8 T cells. These immune responses in tumor microenvironment priming the effector T cells for anti-PD-1 to release their brake for tumor-killing.

Immune checkpoint blockade with anti-PD-1 antibodies have been approved by US FDA for treatment of recurrent and metastatic tumors. Nevertheless, the majority of patients do not respond to the therapy underscoring the need of strategy to alleviate resistance of suppressive microenvironment to immunotherapy. Usually CpG-ODN monotherapy showed good activities in inducing tumor regression in cancer animal model. However, no CpG-ODN has been approved for cancer treatment so far suggesting that CpG-ODN alone may not sufficient for boosting an efficient antitumor immune response in humans. A cooperative effect of CpG-ODNs and immune checkpoint inhibitors on suppression of tumor growth is demonstrated in this disclosure. This combinational therapy is proven to be capable of treatment for tumors with immune suppressive microenvironment.

The invention claimed is:

1. A pharmaceutical composition for treating cancer, comprising an immune checkpoint blockade and an adjuvant composition; wherein the adjuvant composition comprises at least one CpG-oligodeoxynucleotide; wherein the CpG-oligodeoxynucleotide is CpG-2722 (SEQ ID NO:5), the immune checkpoint blockade is an anti-PD1 antibody.

2. The pharmaceutical composition of claim 1, wherein the cancer possesses resistance to immunotherapy.

3. The pharmaceutical composition of claim 1, wherein the cancer is selected from the group consisting of melanoma, non-small cell lung cancer, renal cell carcinoma, hodgkin lymphoma, head and neck cancer, urothelial carcinoma, hepatocellular carcinoma, and small cell lung cancer.

* * * * *